United States Patent [19]

Gradl et al.

[11] Patent Number: 5,166,452
[45] Date of Patent: Nov. 24, 1992

[54] PROCESS FOR INHIBITING AND DESTROYING PEROXIDES IN DIALKYL ETHERS

[75] Inventors: Reinhard Gradl, Erftstadt; Heinz Erpenbach, Cologne; Norbert Weferling, Hürth; Erhard Jägers, Bornheim, all of Fed. Rep. of Germany

[73] Assignee: Hoechst Aktiengesellschaft, Frankfurt am Main, Fed. Rep. of Germany

[21] Appl. No.: 756,341

[22] Filed: Sep. 6, 1991

[30] Foreign Application Priority Data

Sep. 21, 1990 [DE] Fed. Rep. of Germany ....... 4029875

[51] Int. Cl.$^5$ .............................................. C07C 41/46
[52] U.S. Cl. ..................................... 568/580; 568/581
[58] Field of Search ................................. 568/580, 581

[56] References Cited

U.S. PATENT DOCUMENTS

| | | | |
|---|---|---|---|
| 2,132,019 | 10/1938 | Evans | 568/581 |
| 2,427,658 | 9/1947 | Coleman et al. | 568/580 |
| 3,205,269 | 9/1965 | Friedman | 568/581 |
| 3,324,078 | 6/1967 | Matsui | 568/581 |
| 4,476,238 | 10/1984 | Palmer et al. | |

Primary Examiner—Marianne M. Cintins
Assistant Examiner—John D. Peabody, III
Attorney, Agent, or Firm—Connolly and Hutz

[57] ABSTRACT

A process for inhibiting and destroying peroxides in dialkyl ethers having the general formula $R_1OR_2$ in which $R_1$ and $R_2$ are alkyl groups having 1 to 6 carbon atoms, which comprises adding, as inhibitor, a quaternary alkyl iodide of the general formula $$[CH_3alk_3P]I$$

to the dialkyl ethers.

3 Claims, No Drawings

PROCESS FOR INHIBITING AND DESTROYING PEROXIDES IN DIALKYL ETHERS

The invention relates to a process for inhibiting and destroying peroxides in dialkyl ethers having the general formula $R_1OR_2$ in which $R_1$ and $R_2$ are alkyl groups having 1 to 6, in particular 2 or 3, carbon atoms.

Ethers are employed in industry as extractants or as reactants in carbonylation reactions.

During transport and interim storage, peroxides are formed in dialkyl ethers which can decompose in an explosive manner. Peroxides are inhibited and destroyed in dialkyl ethers by adding free-radical scavengers or reducing agents, such as, for example, 2,6-di-tert-butyl-4-methylphenol, sodium sulfites, iron(II) sulfates, potassium pyrosulfites, triethylenetetramine or sodium thiocarbamate. It is disadvantageous here that these compounds are entrained into the subsequent process as impurities or must be removed before use by distillation or scrubbing.

Peroxides in dialkyl ethers can easily be determined using the Perex Test ®, published by E. Merck, Postfach 41 19, 6100 Darmstadt 1, Federal Republic of Germany.

The carbonylation of methanol, methyl acetate or dimethyl ether gives polymeric, tar-like by-products which reduce the effectiveness of noble-metal catalysts and must therefore be purged from the process without losses of noble metal. DE 3 220 226 C2 (U.S. Pat. No. 4,476,238) describes an extractive removal of the noble-metal catalyst from the polymeric, tar-like by-product by means of dialkyl ethers.

The object was to indicate a process for inhibiting and destroying peroxides in dialkyl ethers having the general formula $R_1OR_2$ in which $R_1$ and $R_2$ are alkyl groups having 1 to 6 carbon atoms which prevents the entraining of foreign compounds.

Surprisingly, it has now been found that peroxides in dialkyl ethers are effectively inhibited and destroyed if, as inhibitor, a quaternary alkyl iodide of an element of the fifth main group of the Periodic Table of the Elements is added to the dialkyl ethers.

The process of the invention may furthermore preferably and optionally have the following features:
a) phosphorus, nitrogen or arsenic is selected from the elements of the fifth main group of the Periodic Table of the Elements;
b) a quaternary alkyl iodide of the general formula

[CH$_3$alk$_3$P]I, 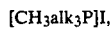

in which alk is an alkyl group having 1 to 16, preferably 4 to 8, carbon atoms, is added;
c) from 25 to 250 mg, in particular from 50 to 100 mg, of quaternary alkyl iodide/1000 g of dialkyl ether are added as inhibitor to the dialkyl ether;
d) the inhibitor is added as a solution in alcohol, in particular in methanol, ethanol or i-propanol;
e) the inhibitor is added as a from 0.5 to 10% strength by weight, in particular as a from 1 to 5% by weight, alcoholic solution.

A further advantage of the novel inhibition and destruction of peroxides in dialkyl ethers is the optical monitoring of the dialkyl ethers. The amount of iodine formed by peroxide results in a yellow coloration, whose intensity is an indicator of the amount of peroxide.

The examples below illustrate our invention in further detail.

EXAMPLE 1

25 ppm of the indicated methyltrialkylphosphonium iodide (as a 1% strength by weight solution in methanol) are added for every 200 g of peroxide-free diisopropyl ether, and a gentle stream of air is passed over the mixture in a colorless glass flask in sunlight. The peroxide content was determined using the PEREX test.

Table 1 shows the results.

TABLE 1

| Inhibitor [25 mg] | Peroxide content [ppm] Aeration time in days | | | |
|---|---|---|---|---|
| | 0 | 4 | 5 | 6 |
| (CH$_3$)$_4$PI | 0 | 15 | 25 | 50 |
| CH$_3$(n—C$_4$H$_9$)$_3$PI | 0 | 0 | 0 | 50 |
| CH$_3$(n—C$_8$H$_{17}$)$_3$PI | 0 | 0 | 0 | 50 |
| no inhibitor | 0 | 25 | 50 | 60 |

EXAMPLE 2

Example 1 was repeated with the following modifications:

50 ppm of CH$_3$(n—C$_4$H$_9$)$_3$PI (as a 3.5% strength by weight solution in methanol) were added to 150 g of peroxide-free diethyl ether.

TABLE 2

| Amount of inhibitor [ppm] | Peroxide content [ppm] Aeration time in days | | | | | |
|---|---|---|---|---|---|---|
| | 0 | 6 | 12 | 19 | 25 | 37 |
| 50 | 0 | 0 | 0 | 0 | 0 | 0 |
| 0 | 0 | 2 | 50 | 100 | 250 | 500 |

EXAMPLE 3

Example 1 was repeated with the following modifications:

Varying amounts of CH$_3$(n—C$_4$H$_9$)$_3$PI (as a 1% strength by weight solution in methanol) were added in each case to 150 g of peroxide-free diisopropyl ether.

TABLE 3

| Amount of inhibitor [ppm] | Peroxide content [ppm] Aeration time in days | | | | | |
|---|---|---|---|---|---|---|
| | 0 | 6 | 12 | 19 | 25 | 37 |
| 50 | 0 | 0 | 0 | 0 | 0 | 0 |
| 75 | 0 | 0 | 0 | 0 | 0 | 0 |

We claim:
1. A process for inhibiting and destroying peroxide in dialkyl ethers having the general formula $R_1OR_2$ in which $R_1$ and $R_2$ are alkyl groups having 1 to 6 carbon atoms, which comprises adding, as inhibitor, a quaternary alkyl iodide of the general formula

[CH$_3$alk$_3$P]I 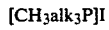

in which alk is an alkyl group having 1 to 16 carbon atoms, in a quantity from 25 to 250 mg of quaternary alkyl iodide/1000 g of dialkyl ether and adding the quaternary alkyl iodide as a solution in alcohol containing 0.5 to 10% strength by weight quaternary alkyl iodide.

2. The process as claimed in claim 1, wherein alk is an alkyl group having 4 to 8 carbon atoms.

3. The process as claimed in claim 1, wherein the alcohol is selected from the group consisting of methanol, ethanol and isopropanol.

UNITED STATES PATENT AND TRADEMARK OFFICE
CERTIFICATE OF CORRECTION

PATENT NO. : 5,166,452

DATED : November 24, 1992

INVENTOR(S) : Gradl et al

It is certified that error appears in the above-indentified patent and that said Letters Patent is hereby corrected as shown below:

On the title page, item [75] Inventors, insert --Andreas Seidel, Köln, Germany--.

Signed and Sealed this

Thirtieth Day of November, 1993

Attest:

Attesting Officer

BRUCE LEHMAN

Commissioner of Patents and Trademarks